(12) United States Patent
Lin et al.

(10) Patent No.: US 11,950,771 B2
(45) Date of Patent: Apr. 9, 2024

(54) SUPPORTING HOOK STRUCTURE FOR FEMORAL SURGERY

(71) Applicant: UNITED ORTHOPEDIC CORPORATION, Hsinchu (TW)

(72) Inventors: Yan-Shen Lin, Hsinchu (TW); Jiann-Jong Liau, Hsinchu (TW); Yu-Liang Liu, Hsinchu (TW); Teh-Yang Lin, Hsinchu (TW); Wen-Chuan Chen, Hsinchu (TW)

(73) Assignee: UNITED ORTHOPEDIC CORPORATION, Hsinchu (TW)

( * ) Notice: Subject to any disclaimer, the term of this patent is extended or adjusted under 35 U.S.C. 154(b) by 333 days.

(21) Appl. No.: 17/402,721

(22) Filed: Aug. 16, 2021

(65) Prior Publication Data

US 2022/0370060 A1    Nov. 24, 2022

(30) Foreign Application Priority Data

May 20, 2021    (TW) .................................. 110118332

(51) Int. Cl.
| | |
|---|---|
| *A61B 17/02* | (2006.01) |
| *A61B 90/00* | (2016.01) |
| *A61F 2/46* | (2006.01) |
| *A61B 17/00* | (2006.01) |

(52) U.S. Cl.
CPC ............ *A61B 17/025* (2013.01); *A61B 90/03* (2016.02); *A61F 2/4607* (2013.01); *A61B 2017/00367* (2013.01); *A61B 2017/0275* (2013.01)

(58) Field of Classification Search
CPC ............ A61B 2017/0275; A61B 17/02; A61B 2017/00464
See application file for complete search history.

(56) References Cited

U.S. PATENT DOCUMENTS

| | | | | |
|---|---|---|---|---|
| 569,839 | A * | 10/1896 | Roeloffs ................ | A61B 17/02 600/219 |
| 3,749,088 | A * | 7/1973 | Kohlmann ......... | A61B 17/0293 74/540 |
| 3,840,014 | A * | 10/1974 | Ling .................... | A61B 17/025 606/90 |
| 4,934,352 | A * | 6/1990 | Sullivan, Jr. ........... | A61B 17/02 600/226 |
| 4,995,875 | A * | 2/1991 | Coes ...................... | A61B 17/02 600/210 |

(Continued)

*Primary Examiner* — David W Bates
(74) *Attorney, Agent, or Firm* — Locke Lord LLP; Tim Tingkang Xia, Esq.

(57) ABSTRACT

The present invention provides a supporting hook structure, comprising a sleeve, a fixing rod, a first limit unit, a hook and a fixing device. The fixing rod is connected to the side surface of the sleeve. The hook body is connected to one end of the sleeve. The first limit unit is arranged on the side surface of the sleeve and adjacent to the hook body. The first limit unit makes the hook body rotates with the axis direction of the sleeve as a rotation axis. The fixing device is connected to the other end of the sleeve to fix the rotating position of the hook body. Through the above, the hook part enters the proximal thigh from a surgical entrance and the hook part rotates to make the hook part abut against the proximal femur to complete the positioning and fixation of the femur hook structure to the femur.

11 Claims, 6 Drawing Sheets

(56) References Cited

U.S. PATENT DOCUMENTS

| | | | | |
|---|---|---|---|---|
| 5,303,694 A * | 4/1994 | Mikhail | A61B 17/02 | 606/208 |
| 5,512,038 A * | 4/1996 | O'Neal | A61B 17/0206 | 600/210 |
| 5,882,298 A * | 3/1999 | Sharratt | A61B 17/02 | 600/210 |
| 5,931,777 A * | 8/1999 | Sava | A61B 17/02 | 600/210 |
| 5,984,865 A * | 11/1999 | Farley | A61B 17/02 | 600/213 |
| 6,860,850 B2 * | 3/2005 | Phillips | A61B 17/02 | 600/210 |
| 7,389,710 B2 * | 6/2008 | Phillips | A61B 17/02 | 74/577 M |
| 7,753,844 B2 * | 7/2010 | Sharratt | A61B 17/0206 | 600/231 |
| 8,360,971 B2 * | 1/2013 | Farley | A61B 17/02 | 600/215 |
| 9,848,862 B2 * | 12/2017 | Bass | A61B 17/02 | |
| 10,893,855 B2 * | 1/2021 | Truckey | A61B 17/0206 | |
| 2002/0035314 A1 * | 3/2002 | Sharratt | A61B 17/025 | 600/235 |
| 2003/0093078 A1 * | 5/2003 | Ritland | A61B 17/8883 | 606/279 |
| 2008/0228191 A1 * | 9/2008 | Downs | A61B 17/025 | 606/100 |
| 2010/0217089 A1 * | 8/2010 | Farley | A61B 17/02 | 600/213 |
| 2013/0204091 A1 * | 8/2013 | Menendez | A61B 17/02 | 600/228 |
| 2013/0204262 A1 * | 8/2013 | Menendez | A61B 17/02 | 606/89 |
| 2017/0231612 A1 * | 8/2017 | Termanini | A61B 17/025 | 606/90 |
| 2019/0314104 A1 * | 10/2019 | Matta | A61B 46/10 | |
| 2021/0128132 A1 * | 5/2021 | Klement | A61B 17/025 | |
| 2022/0096128 A1 * | 3/2022 | Uribe | A61B 17/8869 | |

* cited by examiner

SUPPORTING HOOK STRUCTURE FOR FEMORAL SURGERY

REFERENCE TO RELATED APPLICATIONS

The present application is based on, and claims priority from, Taiwan application number 110118332, filed May 20, 2021, the disclosure of which is hereby incorporated by reference herein in its entirety.

BACKGROUND OF THE INVENTION

Field of the Invention

The present invention relates to medical equipment for surgical operations, in particular to a supporting hook structure for use during femoral surgery.

Description of the Prior Art

Artificial joint replacement is an important surgical procedure. Artificial joint replacement refers to a substitute of human bones and joints made of metal materials with good bio-compatibility and mechanical properties. The purpose of artificial joint replacement is to replace joints by surgical methods for joints that were damaged by erosion from disease or external force in order to correct lesions, remove pain, and restore movement and essential functions of the joints. After nearly 60 years of clinical practice, the therapeutic effect of artificial joint replacement has been fully affirmed and has developed into a reliable method of treatment.

The conventional method is to insert the front tip of a tool into the joint and the doctor holds the end of the tool and pries open the acetabulum to expose the femoral head. However, this prying method is inconvenient for the doctor to concentrate on, and slippage may occur after the front tip is inserted into the joint thereby causing damage to the hip joint or surrounding tissue.

Currently, the Direct Anterior Approach (DAA) is an increasingly widely used approach for minimal invasive total hip replacement surgery. Compared with traditional surgery, total hip replacement under the DAA approach exposes the hip joint from the gap between the tensor fascia lata and rectus femoris muscle. It has the advantages of less soft tissue damage, faster postoperative recovery, and a shorter hospital stay. The early effect is obvious. At present, there have been a number of large-sample research data showing that total hip replacement under the DAA approach can significantly promote the accelerated recovery of patients after surgery.

In the surgical process for total hip replacement under the DAA approach, the exposure of the proximal femur is a crucial step. The current practice is mainly to place a greater trochanter double prong retractor between the proximal femur and the posterior muscles, using the tensor fascia lata muscle and the skin and other soft tissue complexes as the fulcrum, and pressing the double prongs by levering the tail end and lifting the proximal end of the femur to an incline of about 15 degrees. At present, the corresponding devices in the hospital require a lot of lifting force by hospital personnel for an extended period, which is complex to coordinate and has potential for numerous complications.

This surgical method has numerous drawbacks. During the prying process, the tensor fascia lata muscle will receive a greater force. Some elderly patients have a relatively loose soft tissue structure and pressed by the double-pronged retractor they are prone to phenomena such as muscle tearing and excessive soft tissue damage, so it is very unfavorable for the patient's postoperative rehabilitation and functional exercise.

Also, replacement surgery is mainly carried out through small incisions, which involve the stripping of soft tissues and the cutting of the femoral head. During the operation, the retractor is a very critical surgical tool. The existing pull hooks are usually right-angled pull hooks, which need to be used in conjunction with a percussion device when in use. For specific use, three hands are required. Among them, one hand is used to control the retractor, the other hand is used to control the percussion device, and the third hand is used for percussion, and the retractor needs to match the raised angle of the proximal femur. Also, the tip is attached to the lower part of the greater trochanter of the femur, which is very cumbersome to use, which makes the operating time longer.

SUMMARY OF THE INVENTION

In view of the aforementioned shortcomings, one of the objectives of the present invention is to improve the ease of use of the retractor during the operation, so that the retractor can be quickly attached to the lower part of the femoral trochanter to achieve a supporting effect. The invention provides a supporting hook structure that is used to support the femur in the human body during operation, which includes a sleeve, a fixed rod, a first limiting unit, and a hook body.

One end of the fixing rod is connected to the sleeve.

The first limit unit is arranged on the sleeve.

The hook body includes a hook portion, a connecting portion, and a second limiting unit, one end of the connecting portion is connected with one end of the hook portion, and the second limiting unit is provided at the connecting portion.

When the end of the connecting portion is connected to the sleeve, the first limiting unit is connected to the second limiting unit, so that the hook body is able to rotate with the axial direction of the sleeve as the rotation axis and as a first rotational displacement movement.

Further, the first limiting unit is a limiting protrusion, and the second limiting unit includes a recess and a limiting recess, and the limiting recess is ringed on the side surface of the connecting portion and adjacent to the hook portion, the recess is provided on the side surface of the connecting portion, the recess extends from the other end of the connecting portion in the axial direction and is connected with the limiting recess, and the other end of the connecting portion. When the sleeve is connected, the limiting protrusion moves along the recess to the limiting recess, so that the hook body performs the first rotational displacement movement with the axis direction as the rotation axis.

Further, the sleeve includes a first through hole, a second through hole, and a third through hole. The first through hole and the second through hole are respectively located on both ends of the sleeve. The third through hole is located on the side of the sleeve and is adjacent to the first through hole. The first through hole, the second through hole, and the third through hole are in communication with each other, and the limiting protrusion unit is disposed on the third through hole. The limiting protrusion unit protrudes from the inner wall of the first through hole.

Furthermore, the supporting hook structure further includes a fixing device, and the hook body further includes a first recess disposed at an end of the connecting portion.

The fixing device comprises a knob and a fixing bolt, the fixing knob has a second recess, one end of the fixing bolt is connected to the second recess, when the fixing device is inserted into the second through hole with the fixing bolt from the axial direction, and the other end of the fixing bolt is located in the first recess, so that the hook body can perform in a swinging unfixed state.

Further, when the other end of the fixing bolt is located in the first recess, away from the second through hole, and the fixing knob abuts against the sleeve, the hook body is in a fixed state.

In one embodiment, the fixing rod abuts against the second through hole.

Further, the first through hole has a first diameter and the second through hole has a second diameter, the first diameter being greater than the second diameter.

Further, the recess has a first width and the limiting protrusion unit has a second width, and the first width is greater than or equal to the second width.

Further, the recess has a first depth and the limiting recess has a second depth, and the second depth is greater than or equal to the first depth.

Furthermore, the limiting protrusion unit is at a distance from the inner wall of the first through hole, and the distance is less than or equal to the first depth.

In addition, in one embodiment, the other end of the fixed rod has an end portion, and the end portion can be inserted into a hole of a movable base, so that the supporting hook structure supports the femur of the human body.

Further, the fixing rod further includes a fixing ring disposed on the outer wall of the fixing rod and adjacent to the end, and the fixing ring restricts the depth of the fixing rod inserted into the hole.

In another embodiment, the hook has a hook body and an arc portion, both ends of the hook body are respectively connected to the connecting portion and the arc portion, and the hook body is connected to the shaft center at a connection angle between 30 degrees and 90 degrees.

Further, the inner wall of the first recess has a first thread, the outer surface of the fixing bolt has a second thread, and the first thread and the second thread are combined with each other so that the fixing device and the hook body are connected.

Furthermore, the inner wall of the second recess has a third thread, and the second thread and the third thread are combined with each other, so that the fixing knob is connected with the fixing bolt.

In summary, the advantages of the present invention are:

1. The supporting hook structure of the present invention does not need to be divided into a dedicated left or right side orientation. The hook enters the proximal thigh from a surgical entrance and penetrates into the gap between the muscles. The hook can swing to make the hook part transferred underneath the proximal femur to complete the positioning of the femoral hook structure with the femur. There is no need to adapt to the process of attaching to the hook at a specific angle, which can avoid injury such as muscle tears or excessive soft tissue damage.

That is to say, in actual operation, for example, the supporting hook structure of the present invention with the lifting mechanism and with the movable design of the hook can immediately adjust itself to the most appropriate angle in real-time as the operating position changes, avoiding the support from surface contact to point contact and causing an unfavorable damage such as muscle tears or excessive soft tissue damage.

2. When the positioning has been completed, the hook body is fixed by the fixing device, and the fixing rod is inserted into the hole of the movable base, so that the supporting hook structure supports the femur in the human body and prevents the hook from deviating from the positioning angle due to external force.

In addition, the advantage of this fixing device is that it can be fixed or unfixed. Choosing the fixed state is in line with the current needs of the operation and can maintain stability; choosing the unfixed state (swinging) can promptly respond to any force conditions to make the hook swing and self-adjust the angle. With the above, the doctor can choose whether to fix or not according to the situation while performing the operation.

DESCRIPTION OF THE PREFERRED EMBODIMENTS

In order to make the purpose, technical solutions, and advantages of this application clearer, the application will be further described in detail below with reference to the drawings and embodiments. It should be understood that the specific embodiments described here are only used to explain the present application, and are not used to limit the present application.

Figure 1:
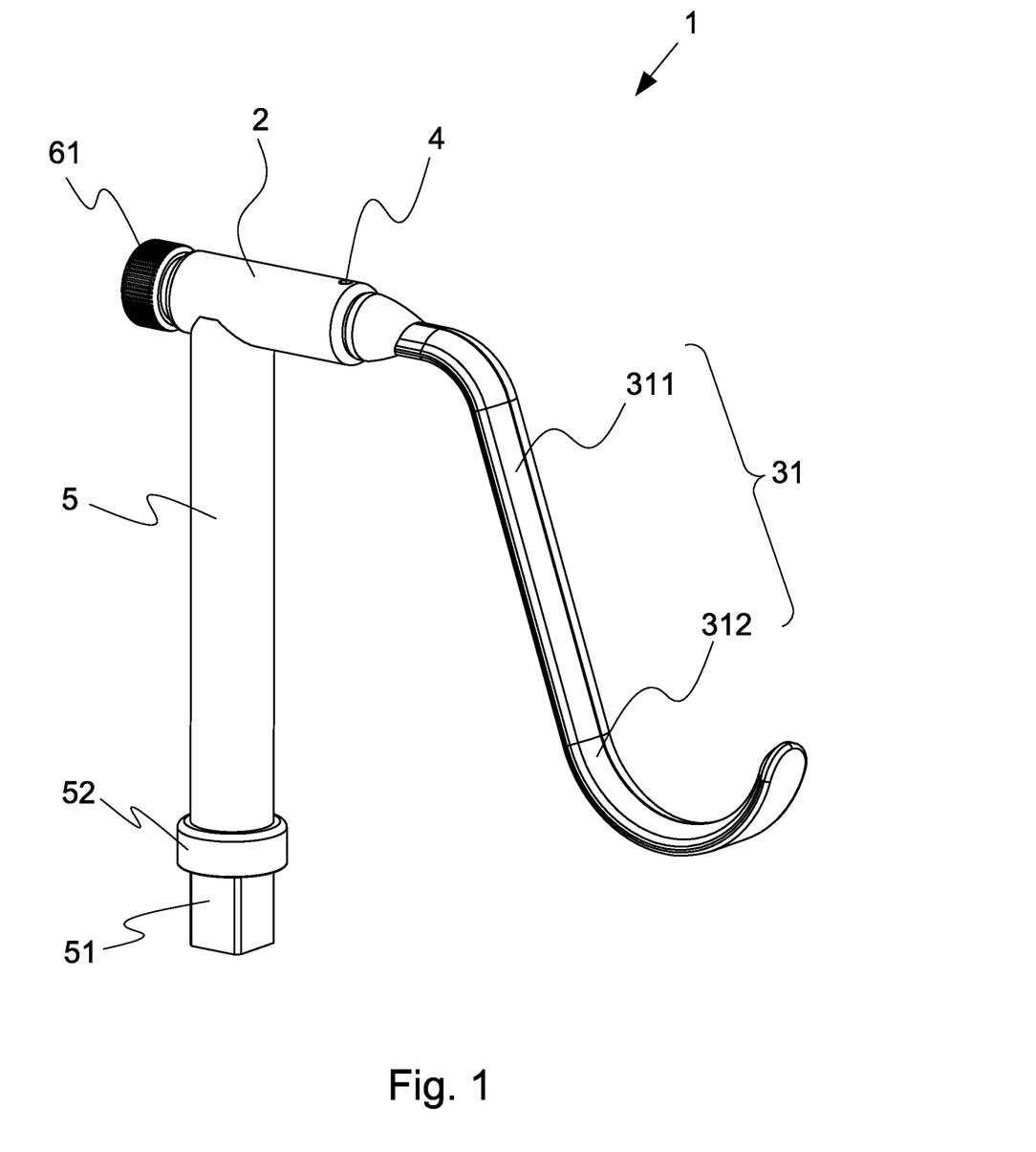
FIG. 1 is a three-dimensional schematic diagram of the supporting hook structure of the present invention.
Figure 2:
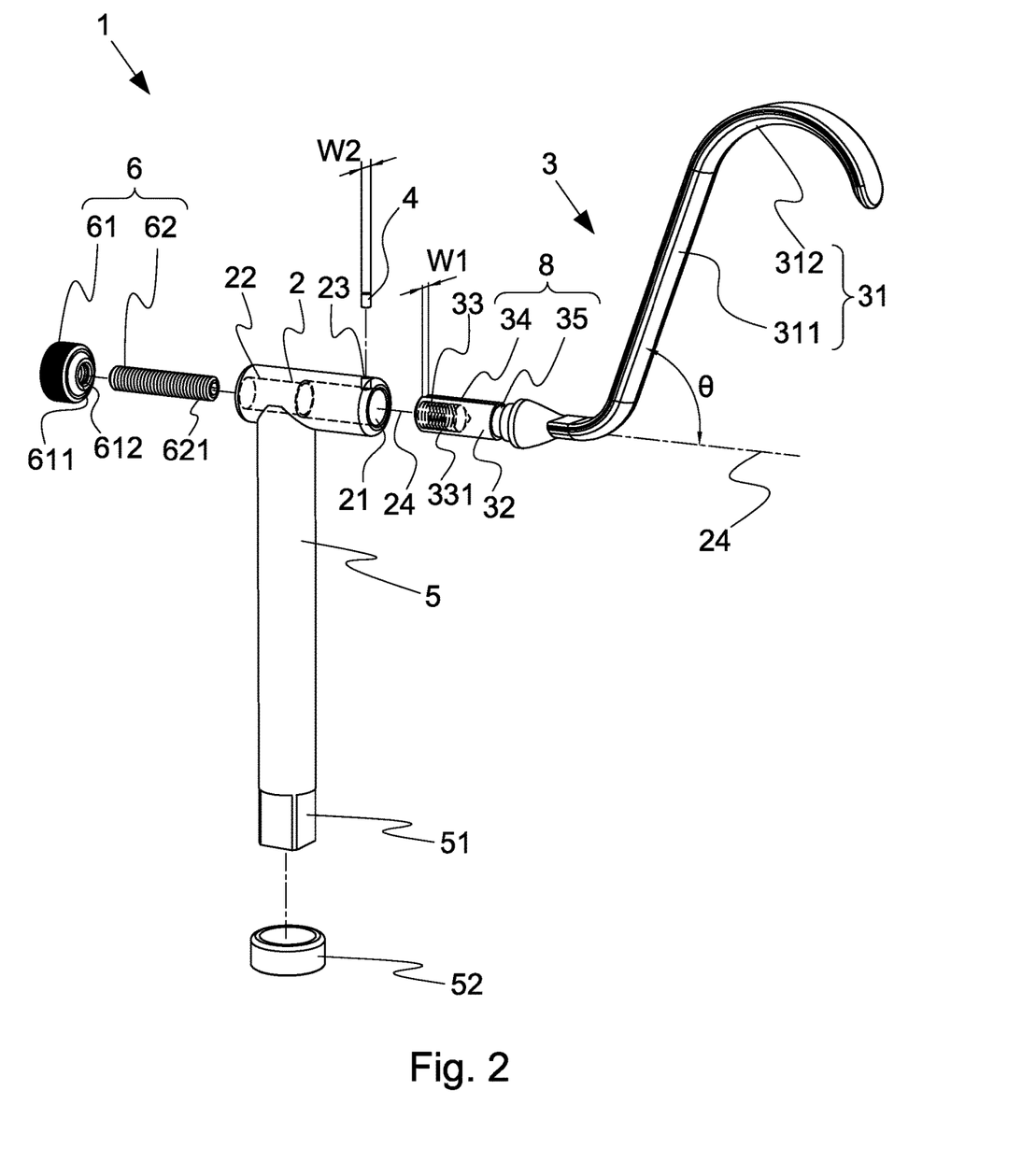
FIG. 2 is a three-dimensional exploded schematic view of the supporting hook structure of the present invention.
Figure 3:
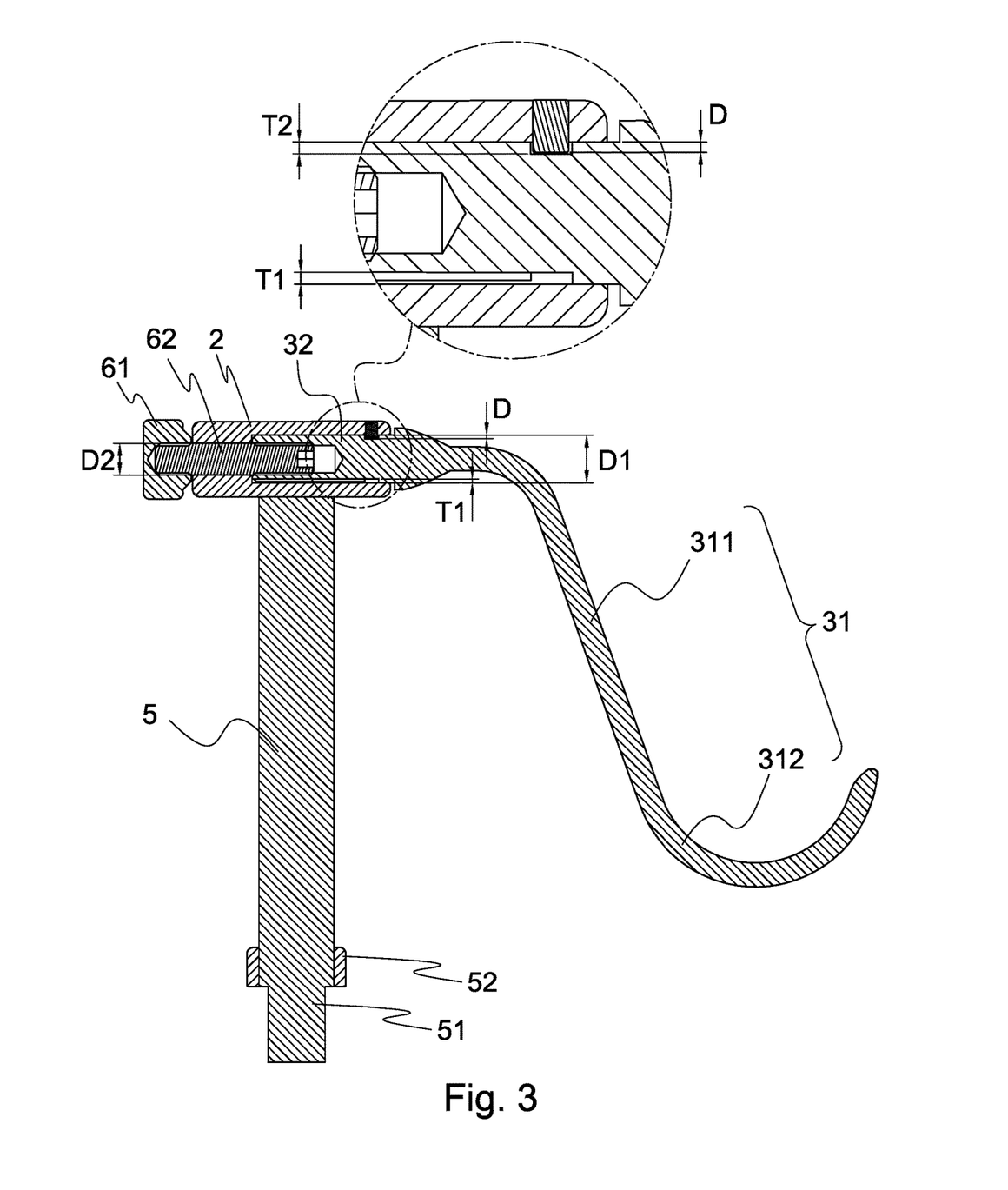
FIG. 3 is a schematic cross-sectional view of the supporting hook structure of the present invention.

Please refer to FIGS. 1, 2, and 3, the present invention provides a supporting hook structure 1 for supporting the femur in the human body during surgery, which includes a sleeve 2, a hook body 3, and a first limiting unit 4, a fixing rod 5 and a fixing device 6.

The sleeve 2 includes a first through hole 21, a second through hole 22, and a third through hole 23. The first through hole 21 and the second through hole 22 are respectively located on the two ends of the sleeve 2. On the end surface area, the third through hole 23 is located on the side surface of the sleeve 2 and is adjacent to the first through hole 21, and the first through hole 21, the second through hole 22, and the third through hole 23 are in relation with each other.

In a preferred embodiment, the first through hole 21 has a first diameter D1 and the second through hole 22 has a second diameter D2, the first diameter D1 is greater than the second diameter D2, and as a result, the hook body 3 can only be inserted through the first through hole 21, and the fixing device 6 can only be inserted through the second through hole 22, which prevents the user from making mistakes during assembly.

The hook body 3 includes a hook portion 31, a connecting portion 32, a second limiting unit 8 and a first recess 33. In a preferred embodiment, the second limiting unit 8 includes a recess end 34 and a limiting recess 35, one end of the connecting portion 32 is connected to one end of the hook portion 31, the first recess 33 is provided at the other end of the connecting portion 32, and the recess end 34 is provided on the connecting portion 32, the recess end 34 extends from the other end of the connecting portion 32 in the axial direction 24 of the sleeve 2 and is connected to the limiting recess 35, the recess end 34 has a first width W1 and A first depth T1, the limiting recess 35 is circumferentially arranged on the side surface of the connecting portion 32 and adjacent to the hook portion 31, and the limiting recess 35 has a second depth T2.

In the present preferred embodiment, the hook portion 31 has a hook body portion 311 and an arc portion 312, both ends of the hook body portion 311 are respectively connected to the connecting portion 32 and the arc portion 312, the hook body portion 311 is connected with the axial direction 24 to have an angle θ between 0 degrees and 90 degrees, preferably, the angle θ is between 30 degrees and 90 degrees.

The first limiting unit 4 is disposed in the third through hole 23, the first limiting unit 4 has a second width W2 and the first limiting unit 4 protrudes into the first through hole 21 within a distance D from the wall.

One end of the fixing rod 5 is connected to the side surface of the sleeve 2, and the fixing rod 5 abuts against the second through hole 22.

The fixing device 6 includes a fixing knob 61 and a fixing bolt 62. The fixing knob 61 has a second recess 611, and one end of the fixing bolt 62 is connected to the second recess 611.

In the above, in this preferred embodiment, the first width W1 is greater than or equal to the second width W2, and the distance D is less than or equal to the first depth T1, so that when the connecting portion 32 is from the axial direction 24 when inserted into the first through hole 21, the first limiting unit 4 moves along the recess 34 to the limiting recess 35.

In addition, the second depth T2 is greater than or equal to the first depth T1, so that after the first limiting unit 4 is moved to the limiting recess 35, the hook body 3 takes the axial direction 24 as the rotation axis to perform a first rotational displacement movement 91.

Figure 4:
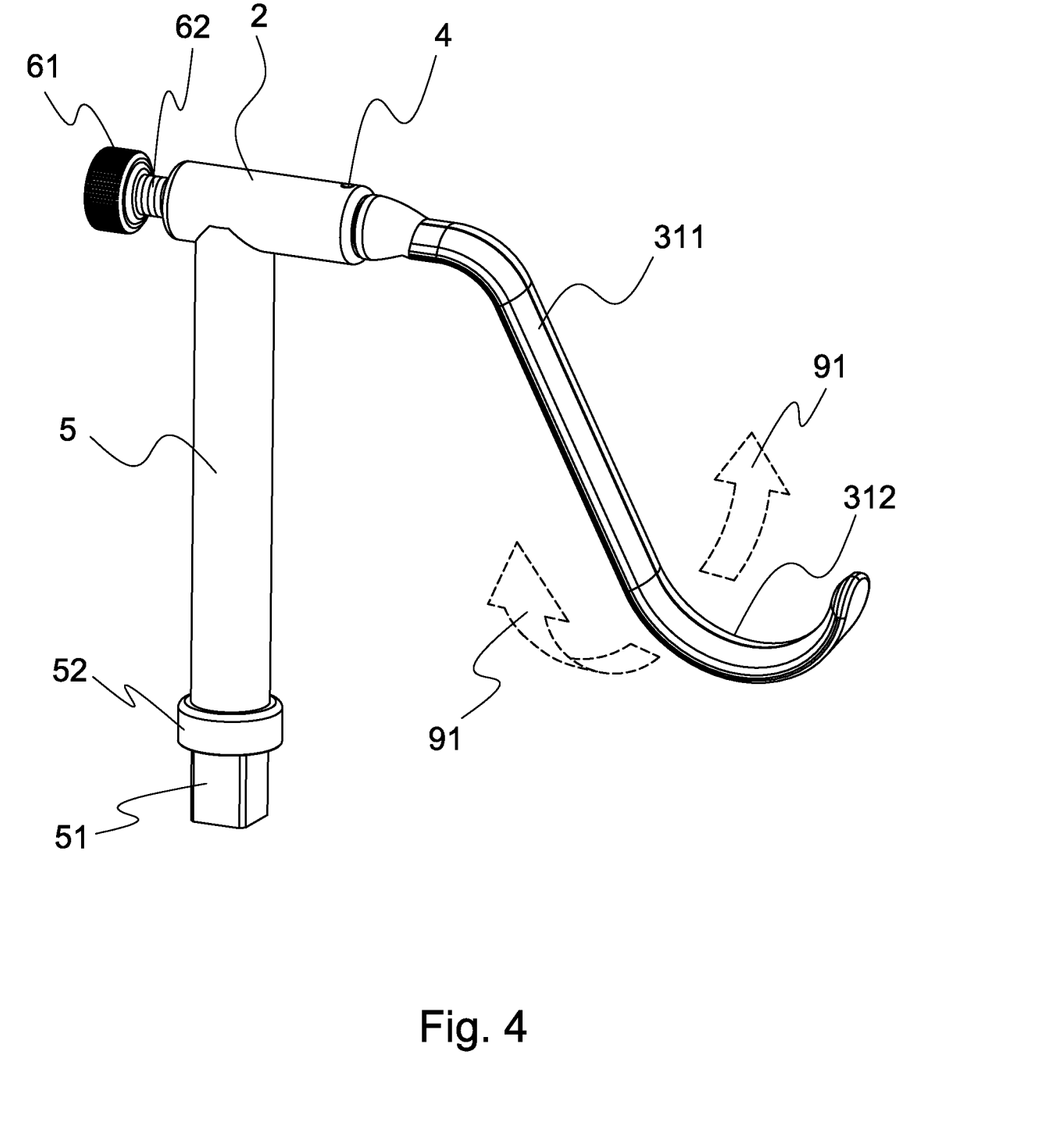
FIG. 4 is a schematic diagram of the hook body of the present invention in an unfixed swinging state.
Figure 5:
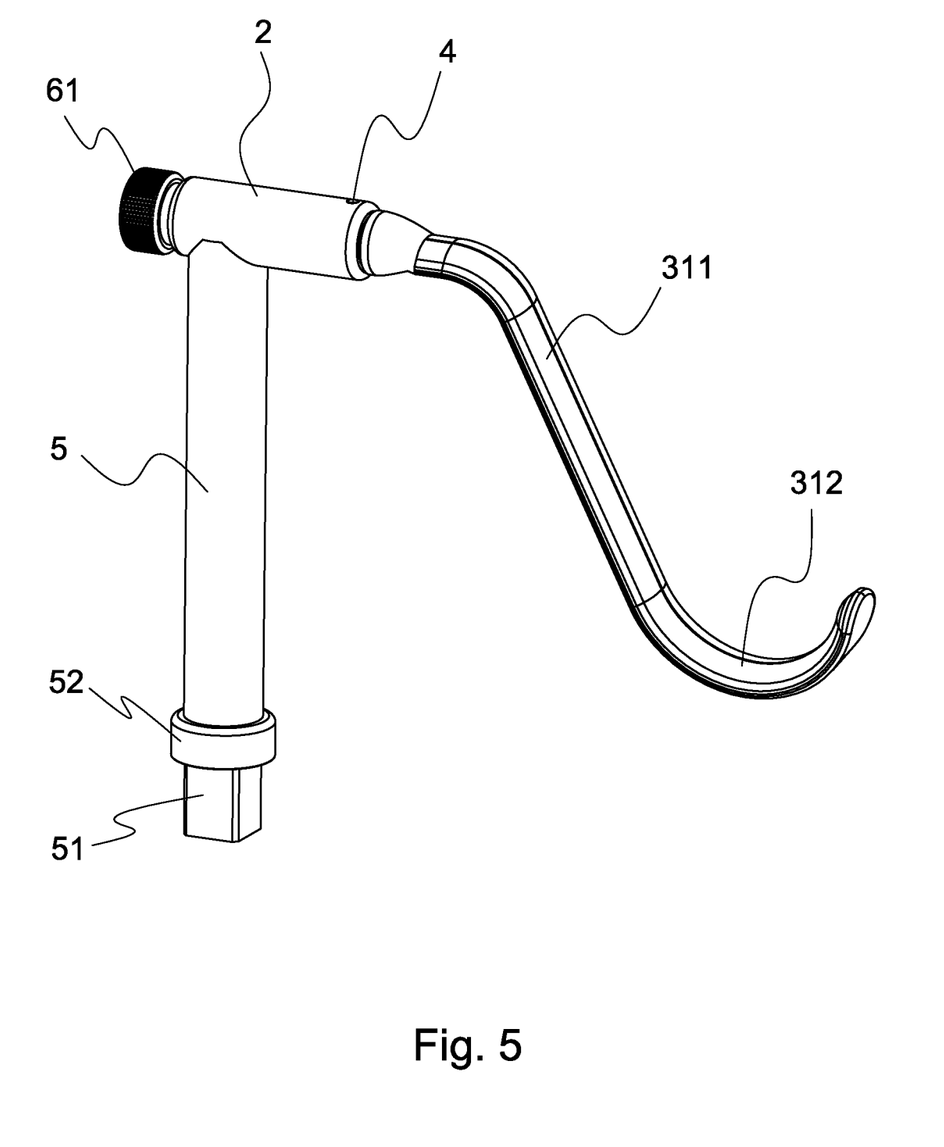
FIG. 5 is a schematic diagram of the hook body of the present invention in a fixed state.

When the fixing device 6 inserts the fixing bolt 62 into the second through hole 22 from the axial direction 24, and the other end of the fixing bolt 62 is located in the first recess 33, the hook body 3 is located in a swing state (as shown in FIG. 4); when the other end of the fixing bolt 62 is located in the first recess 33, away from the second through hole 22, and the fixing knob 61 abuts against the sleeve 2, the hook body 3 is in a fixed state (as shown in FIG. 5).

It is further explained that in the unfixed swinging state, the hook body 3 can rotate freely in a clockwise or counterclockwise direction with the axial direction 24 of the sleeve 2 as the rotation axis, and the hook body 3 is movable and the design can immediately adjust itself to the most appropriate angle as the operating position changes in real-time, avoiding the disadvantage of the support from surface contact to point contact, and cause muscle tears or excessive soft tissue damage.

In addition, when the hook body 3 is not completely fixed, the supporting hook structure 1 can be retained during operation (when the femur is lifted), the adjustment function is accompanied by the lifting mechanism, and when the femur is lifted or lowered, the hook body 3 can achieve a self-adjusting function by rotating according to rising or falling movement.

As the fixing knob 61 is rotated, the fixing pin 62 in the axial direction 24 moves from the first recess 33 opening depth of the first recess 33, until the fixing knob 61 abuts on the sleeve of the barrel 2 and enables the fixing device 6 to be fixed to the first recess 33, so that the hook body 3 is located at a fixed position and is in a fixed state.

Figure 6:
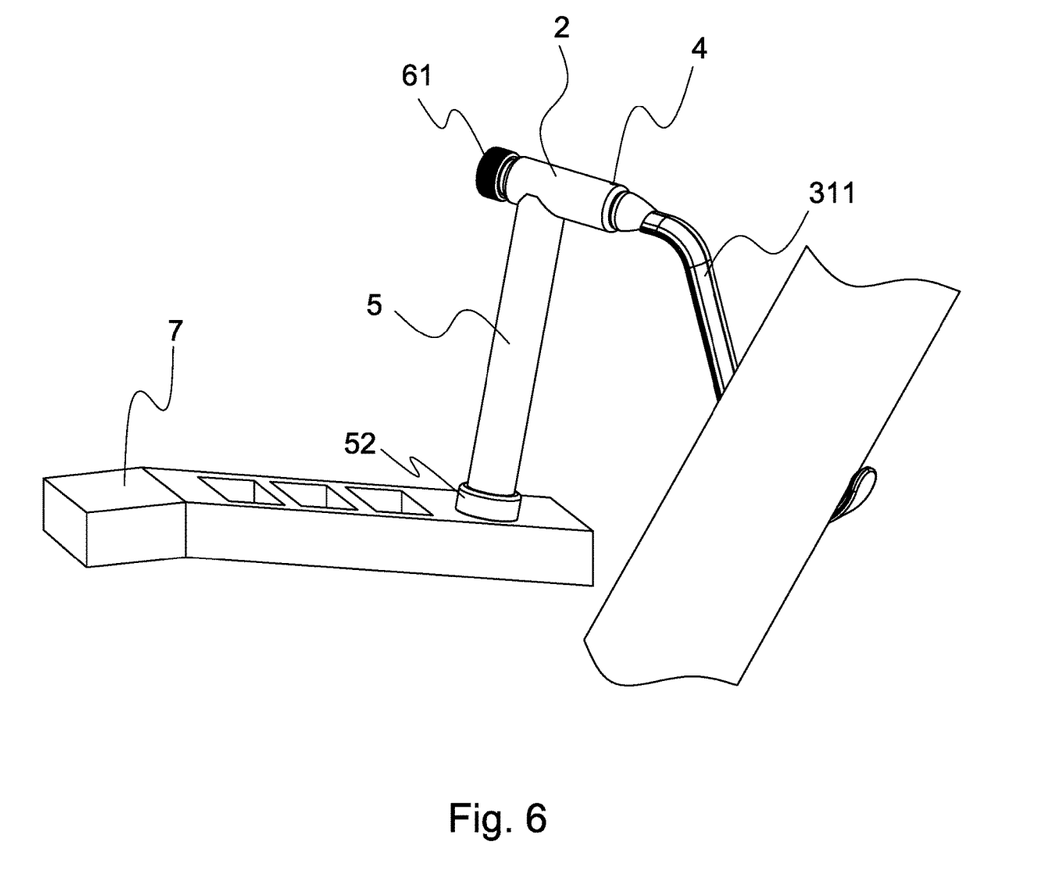
FIG. 6 is a three-dimensional schematic diagram of the supporting hook structure of the present invention.

In addition, in the preferred embodiment according to the present embodiment, the end of the fixing rod 5 has an end portion 51, and the end portion 51 can be inserted into a movable base 7 such that the supporting hook structure 1 to support the femur in the patient's body.

That is to say, first the hook 31 enters the proximal thigh from the surgical entrance and penetrates into the gap of the muscles, and the hook 31 is transferred under the proximal femur through the first rotational movement 91, and on completion of the positioning of the femur, by the fixing knob 61 moving until it is against the second through-hole 22, the hook 3 is in the fixed state, and the end portion 51 is inserted into a hole in the movable base 7, and then the supporting hook structure supports the femur in the human body (as shown in FIG. 6).

Preferably, the fixing rod 5 further includes a fixing ring 52, the fixing ring 52 is arranged on the outer wall of the fixing rod 5 and abuts the end 51, and the fixing ring 52 restricts the depth and movement of the fixing rod 5 when it is inserted into the hole of the movable base 7.

Furthermore, in the above-mentioned preferred embodiment, the inner wall of the first recess 33 has a first thread 331, and the outer surface of the fixing bolt 62 has a second thread 621, and the first thread 331 in combination with the second thread 621 have a mating arrangement to allow the fixing device 6 to connect to the hook body 3, and the inner wall of the second recess 611 has a third thread 612. The second thread 621 and the third thread 612 combine with each other, and thereby the fixing knob 61 and the fixing bolt 62 are connected.

In summary, the advantages of the present invention are:

1. The supporting hook structure of the present invention does not need to be divided into a dedicated left or right side orientation. The hook enters the proximal thigh from a surgical entrance and penetrates into the gap between the muscles. The hook can swing to make the hook part transferred underneath the proximal femur to complete the positioning of the femoral hook structure with the femur. There is no need to adapt to the process of attaching to the hook at a specific angle, which can avoid injury such as muscle tears or excessive soft tissue damage.

That is to say, in actual operation, for example, the supporting hook structure of the present invention with the lifting mechanism and with the movable design of the hook can immediately adjust itself to the most appropriate angle in real-time as the operating position changes, avoiding the support from surface contact to point contact and causing an unfavorable damage such as muscle tears or excessive soft tissue damage.

2. When the positioning has been completed, the hook body is fixed by the fixing device, and the fixing rod is inserted into the hole of the movable base, so that the supporting hook structure supports the femur in the human body and prevents the hook from deviating from the positioning angle due to external force.

In addition, the advantage of this fixing device is that it can be fixed or unfixed. Choosing the fixed state is in line with the current needs of the operation and can maintain stability; choosing the unfixed state (swinging) can promptly respond to any force conditions to make the hook swing and self-adjust the angle. With the above, the doctor can choose whether to fix or not according to the situation while performing the operation.

The above embodiments are only used to illustrate the technical solutions of the present invention and not to limit them. Although the present invention has been described in detail with reference to the preferred embodiments, those of ordinary skill in the art should understand that the technical solutions of the present invention can be modified or modified. Equivalent replacement without departing from the spirit and scope of the technical solution of the present invention.

What is claimed is:

1. A supporting hook structure, which includes:
   a sleeve;
   a fixing rod, one end of the fixing rod is connected to the sleeve;
   a first limiting unit, the first limiting unit is arranged on the sleeve; and
   a hook body, the hook body includes a hook portion, a connecting portion, and a second limiting unit, one end of the connecting portion is connected to one end of the hook portion, and the second limiting unit is provided at the connecting portion;
   wherein, when the end of the connecting portion is connected to the sleeve, the first limiting unit is connected to the second limiting unit, so that the hook body is able to perform a first rotation with an axial direction of the sleeve as the rotation axis;
   wherein the first limiting unit is a limiting protrusion unit, and the second limiting unit includes a recess and a limiting recess, the limiting recess is annularly arranged on the side surface of the connecting portion and adjacent to the hook portion, the recess is arranged on the side surface of the connecting portion, and the recess extends from an end of the connecting portion in an axial direction and is connected to the limiting recess, and when another end of the connecting portion is connected to the sleeve, the limiting protrusion moves along the recess to the limiting recess, so that the hook body is able to perform a rotation with the axis direction as the rotation axis;
   wherein the sleeve includes a first through hole, a second through hole, and a third through hole, the first through hole and the second through hole are respectively located on both ends of the sleeve, the third through hole is located on the side of the sleeve and is adjacent to the first through hole, and the first through hole, the second through hole, and the third through hole are in communication with each other, the limiting protrusion unit is disposed in the third through hole, and the limiting protrusion unit protrudes from the inner wall of the first through hole;
   wherein the supporting hook structure further includes a fixing device, and the hook body further includes a first recess, and the first recess is disposed on the end of the connecting portion, the fixing device includes a fixing knob and a fixing bolt, the fixing knob has a second recess, one end of the fixing bolt is connected to the second recess, and inserted in the axial direction into the second through hole, and the other end of the fixing bolt is located in the first recess, so that the hook body is in an unfixed swing state;
   wherein the inner wall of the first recess has a first thread, and the outer surface of the fixing bolt has a second thread, and combined with the second thread, the fixing device is connected with the hook body.

2. The supporting hook structure according to claim 1, wherein when the end of the fixing bolt is located in the first recess, away from the second through hole, and the fixing knob abuts against the sleeve, the hook body in a fixed state.

3. The supporting hook structure according to claim 1, wherein the fixing rod abuts against the second through hole.

4. The supporting hook structure of claim 1, wherein the first through hole has a first diameter and the second through hole has a second diameter, the first diameter being greater than the second diameter.

5. The supporting hook structure according to claim 1, wherein the recess has a first width and the limiting protrusion unit has a second width, and the first width is greater than or equal to the second width.

6. The supporting hook structure according to claim 1, wherein the recess has a first depth and the limiting recess has a second depth, and the second depth is greater than or equal to the first depth.

7. The supporting hook structure according to claim 6, wherein the limiting protrusion unit is at a distance from the inner wall of the first through hole, and the distance is less than or equal to the first depth.

8. The supporting hook structure according to claim 1, wherein the end of the fixing rod has an end portion that can be inserted into a hole of a movable base, so that the supporting hook structure supports a femur in a human body.

9. The supporting hook structure according to claim 8, wherein the fixing rod further includes a fixing ring disposed on an outer wall of the fixing rod and adjacent to the end, and the fixing ring restricts the depth of the fixing rod inserted into the hole.

10. The supporting hook structure according to claim 1, wherein the hook has a hook body and an arc portion, and both ends of the hook body are respectively connected to the connecting portion and the arc portion, the connecting angle between the hook body and the axial direction is between 30 degrees and 90 degrees.

11. The supporting hook structure according to claim 1, wherein the inner wall of the second recess has a third thread, and the second thread and the third thread are combined with each other, so that the fixed knob and the fixing bolt is connected.

* * * * *